United States Patent [19]
Yamada et al.

[11] Patent Number: 5,995,137
[45] Date of Patent: Nov. 30, 1999

[54] IMAGE PICKUP APPARATUS

[75] Inventors: Yoshiro Yamada, 1-2-12-403, Kaname-cho, Toshima-ku, Tokyo 171; Mikio Saito, Tokyo, both of Japan

[73] Assignee: Yoshiro Yamada, Tokyo, Japan

[21] Appl. No.: 08/649,644

[22] PCT Filed: Nov. 24, 1994

[86] PCT No.: PCT/JP94/01981

§ 371 Date: May 23, 1996

§ 102(e) Date: May 23, 1996

[87] PCT Pub. No.: WO95/15055

PCT Pub. Date: Jun. 1, 1995

[30] Foreign Application Priority Data

Nov. 24, 1993 [JP] Japan .................................... 5/293527

[51] Int. Cl.⁶ .................................................. H04N 7/18
[52] U.S. Cl. ............................................ 348/88; 358/454
[58] Field of Search ..................................... 348/340, 219, 348/97, 88, 342; 358/454, 451, 453, 463, 516, 523; 359/679, 683

[56] References Cited

U.S. PATENT DOCUMENTS

| 4,660,091 | 4/1987 | Nutting ..................................... 348/97 |
| 4,812,915 | 3/1989 | Tada . |
| 4,893,195 | 1/1990 | Tada et al. .............................. 358/454 |
| 4,939,590 | 7/1990 | Tada . |
| 4,951,223 | 8/1990 | Wales et al. ............................. 348/88 |
| 5,007,719 | 4/1991 | Hasegawa . |
| 5,294,973 | 3/1994 | Byrne ......................................... 348/88 |
| 5,402,171 | 3/1995 | Tagami et al. .......................... 348/219 |
| 5,440,648 | 8/1995 | Roberts et al. ............................ 348/88 |
| 5,450,243 | 9/1995 | Nishioka ................................. 348/340 |
| 5,461,418 | 10/1995 | Shiraishi ................................. 348/342 |

FOREIGN PATENT DOCUMENTS 0416114  3/1991  European Pat. Off. .

OTHER PUBLICATIONS

Osugi Michio, Patent Abstracts of Japan, vol. 17, No. 192, Nov. 26, 1992 (Exhibit 5).

Primary Examiner—Bryan Tung
Assistant Examiner—Gims S. Philippe
Attorney, Agent, or Firm—John P. White; Cooper & Dunham LLP

[57] ABSTRACT

An image pickup system including an image pickup device (4) for taking an image from an object (1) containing a periodic pattern and outputting an image signal (5), a zoom lens (2) for forming an object image on the image pickup device, a moire amount detection circuit (10) for detecting an amount of moire from the image signal (5), and an imaging magnification control circuit including a differentiating circuit (18) provided for setting a magnification of the zoom lens (2) and finely adjusting the magnification of the zoom lens (2) to allow the amount of moire detected by the moire amount detection circuit (10) to become below the setting value, a positive/negative determination circuit (20), a system controller (22), and a ROM (24).

20 Claims, 8 Drawing Sheets

IMAGE PICKUP APPARATUS

TECHNICAL FIELD

The present invention relates to an image pickup apparatus and, in particular, to an image pickup apparatus applied to a defect checking apparatus for checking a defect on a target object having a periodic pattern, such as a fabric, shadow mask and liquid crystal panel, and to a television camera (TV camera) for taking an image containing a periodic pattern.

BACKGROUND ART

The fabric used for bags, shoes, conveyors, etc., is manufactured by a weaving machine and has a periodic pattern such as lattice—or interdigital-stripes. Here it is to be noted that various defects unavoidably occur to a certain extent in these fabrics depending upon the homogeneity of those materials, working conditions, soiled spots in the manufacturing process.

On the other hand, other products having a periodic pattern are, for example, a shadow mask used in color CRTs and a liquid crystal panel used for liquid crystal display. The shadow mask is used as a color separation mechanism for the color CRT and comprised of an alloy plate with a periodic array of many fine openings for a plurality of color components provided to allow passage of electron beams of respective color components. The liquid crystal panel is so constructed as to have a matrix array of many pixels. These products, such as a shadow mask and liquid crystal panel, sometimes suffer various defects in the manufacturing process.

The checking of defects in the products with a periodic pattern has been made by human eye.

In recent years, a defect checking apparatus has been developed which automatically checks defects by taking an image from an object with a periodic pattern by means of a camera using a solid-state image pickup device such as a OCD image sensor and performing processing on an image signal obtained.

Taking the fabric as an example of an object, checking of a defect of a relatively large contrast, such as hole openings, burning marks, can be effected relatively easily on the conventional defect checking apparatus. However, it has been difficult to check microdefects specific to the fabric. That is, if the pixel pitch of the image pickup device is made finer to accurately check such a microdefect, then a moire pattern emerges as the size of the pixel gets nearer to a lattice of a periodic pattern of the object. If such a moire pattern appears, it becomes difficult to check the object for defects and this provides a bar to the detection of them.

Even on a TV camera such as a business TV camera for broadcasting in particular, a high quality video camera for a general consumer and an HDTV (high definition television) camera, if an image is taken from an object including a striped fabric having a fine periodic pattern, a moire interference emerges.

In order to avoid such a moire pattern, a conventional method is known by which the high component of a spatial frequency involved is cut off by inserting an optical lowpass filter in an incident light path of the image pickup device. However, this method involves a lowering in image resolution. That is, with the optical lowpass filter inserted, very fine information of the high component of the spatial frequency is sacrificed so that such a camera cannot be applied to a defect checking apparatus of high precision adapted to check such a microdefects as set out above. For the TV camera, the lowering of the resolution would lead to the degeneration of an image quality.

It is accordingly an object of the present invention to provide an image pickup apparatus applicable to a defect checking apparatus and TV camera capable of effectively eliminating moire interference without sacrificing an image resolution.

DISCLOSURE OF THE INVENTION

An image pickup apparatus according to the present invention comprises an image pickup device for taking an image from an object containing a periodic pattern and for outputting an image signal, image processing means for processing the image signal output from the image pickup device, and imaging magnification setting means for setting an imaging magnification of the object relative to the image pickup device in accordance with the pitch of the periodic pattern contained in the object.

The image pickup apparatus according to the present invention further comprises, in addition to the above-mentioned arrangement, an imaging magnification setting means for setting the imaging magnification of the object relative to the image pickup device, amount of moire detection means for detecting an amount of moire from the image signal, and imaging magnification adjusting means for adjusting the imaging magnification set by the imaging magnification setting means so that the amount of moire detected by the amount of moire detecting means is made lower than the setting value.

Generally, the image pickup device is structured in a one- or two-dimensional array with a plurality of pixels arranged at a predetermined pitch. In the case where the image is taken by the image pickup device from the object having the periodic pattern, a moire pattern emerges if the pixel pitch of the image pickup device is nearer to that of the periodic pattern imaged on the image pickup device. However, the moire pattern becomes zero by setting the pixel pitch in a way to have an integral multiple of the pitch of the periodic pattern imaged on the image pickup device. Further, when, in particular, the pixel pitch has a double relation to the pitch of the periodic pattern imaged on the image pickup device, the highest resolution is obtained in a range in which no moire pattern emerges.

The pixel pitch of the image pickup device cannot be varied but the pitch of the periodic pattern imaged on the image pickup device can be varied by varying the imaging magnification of the object relative to the image pickup device.

With attention paid to this point, according to the present invention, the moire pattern is reduced by properly setting the imaging magnification in a way to correspond to the pitch of the periodic pattern on the object. In this case, it is not necessary to set the moire pattern to completely zero and it is sufficient if being made at a level lower than that detectable by the human eye. It is not necessary that the pixel pitch be made precisely an integral multiple relation to the pitch of the periodic pattern imaged on the image pickup device. The moire pattern is adequately reduced even in that neighboring region. For example, in the case where the object, such as the fabric, contains a variation in pitch of the periodic pattern, it is not necessarily required that, with the imaging magnification fixed, the moire pattern be reduced in all positions on the object. This is also true of the image pickup apparatus, such as the TV camera for broadcasting, etc., taking natural images. Even in an object, such as the shadow mask and liquid crystal panel, with the pitch of the periodic pattern exactly uniform, there are sometimes the cases where irregular pitches occur at the periodic pattern, with an image formed on the image pickup device, due to the deformation of a lens in an optical system by which an image of the object is formed on the image pickup device.

According to the present invention, means is provided whereby, through the detection of the amount of moire from an image signal output from the image pickup device, the image magnification is adjusted so that the detected amount of moire is reduced below a predetermined value, for example, below a detectable limit. By this means it is possible to lower the moire pattern at all areas on the object.

BRIEF DESCRIPTION OF THE DRAWINGS

FIG. 6 shows a variation of a deviation value caused by a positional variation of the pixels when the periodic pattern of FIG. 4 and FIG. 5 is taken at various pixel pitches;

BEST MODE OF CARRYING OUT THE INVENTION

The present invention will be explained below in more detail with reference to the accompanying drawings.

Figure 1:
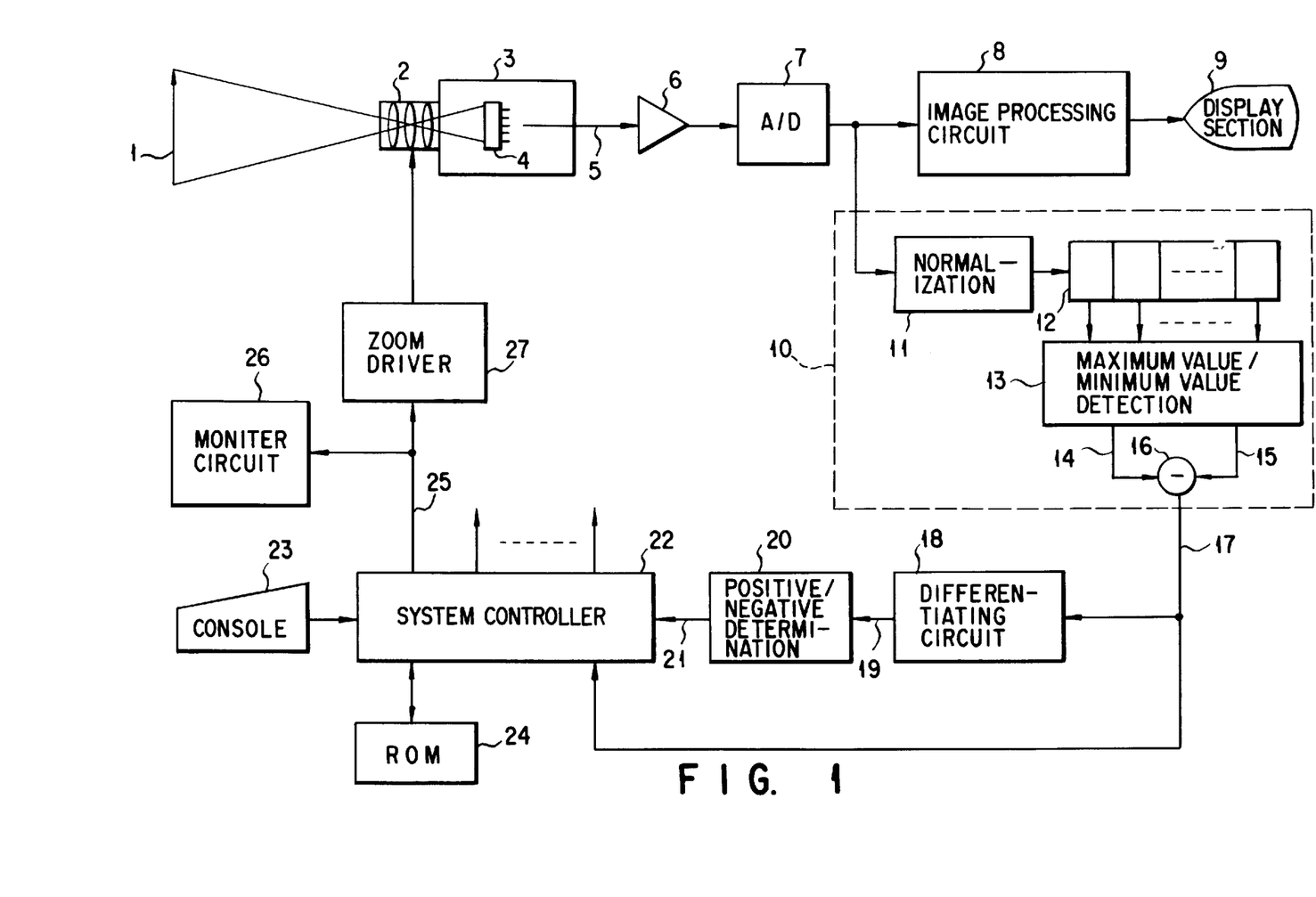
FIG. 1 is a block diagram showing an arrangement of an image pickup apparatus according to one embodiment of the present invention.

The embodiment of the present invention will be explained below by referring to the accompanying drawings. FIG. 1 is a schematic diagram showing an image pickup apparatus according to one embodiment of the present invention.

In FIG. 1, an object 1 including a periodic pattern is comprised of, in the case of a defect checking apparatus, a fabric, shadow mask, liquid crystal panel or other objects to be checked and, in the case of a TV camera for broadcasting for instance, a natural image. An image of the object 1 is formed on an image pickup device 4 in a camera section 3 through a zoom lens of an imaging amplification variable mechanism. The zoom lens 2 is of a magnification variable lens system with a plurality of optical lenses combined together as is well known in the art and driven by a zoom driver 27 with the use of an electric motor as will be set out below to allow a variation of a magnification and, by doing so, a variation of an imaging magnification of the object 1 relative to the image pickup device 4. Such a zoom lens having its magnification controlled by the electric drive source is called a power zoom. The image pickup device 4 is comprised of a solid-state image pickup device, such as a one- or two-dimensional CCD (charged coupled device) image sensor and delivers an electric signal (image signal) 5 corresponding to an image of an object thus formed.

The image signal 5 output from the image pickup device 4, being amplified by an amplifier 6, is input to an A/D converter 7 and converted to digital data (hereinafter referred to as image signal data) of, for example, a 8 bits-per-pixel, that is a 256-level, gradation. The image signal data is input to an image processing section 8 and, being subjected to predetermined processing, supplied to a display section 9, such as a CRT display and liquid crystal display, where it is displayed as an image.

The image signal data output from the A/D converter 7 is also input to a moire amount detection circuit 10.

The moire amount detection circuit 10 is adapted to detect an amount of moire components in the image signal 5 output from the image pickup device 4 and, in this example, comprises a normalization circuit 11 for normalizing the image signal data from the A/D converter 7, a plural-stage shift register 12 for storing data corresponding to a plurality of continuous pixels of normalized image signal data, a maximum value/minimum value detection circuit 13 for detecting maximum and minimum values of the outputs of the stages of the shift register 11, and a subtracter 16 for finding a difference between the maximum value 14 and the minimum value 15 output from the detection circuit 13. The output of the subtracter 16 thus obtained is delivered as an output 17 of the moire amount detection circuit 10. The output 17 is used to represent an amount of moire contained in the image signal 5 output from the image pickup device 1 as will be set out below. Hereinafter, the output 17 of the moire amount detection circuit 10 is referred to as a moire amount signal.

The moire amount signal 17 output from the moire amount detection circuit 10 is input to a differentiating circuit 18. The differentiating circuit 18 finds a differentiated value 19, that is, the slope of a variation of the moire amount signal 17 when the imaging magnification of the zoom lens 2 is minutely varied, and is comprised of, for example, a digital difference device.

The output (differentiated values) 19 of the differentiating circuit 18 is input to a positive/ negative determination circuit 20. The positive/negative determination circuit 20 determines a positive or negative value (including zero) of the differentiated value 19 and a result of determination, 21, is input, together with the moire amount signal 17, to a system controller 22.

The system controller 22 is comprised of a circuit for controlling each part of the image pickup device on the basis of the moire amount signal 17 output from the moire amount detection circuit 10, result of determination by the positive/negative determination circuit 20 and signals from a console 23 and ROM (read-only memory) 24. Here, out of the kinds of controls performed by the system controller 22, the featuring control of the present invention is the control made to the zoom driver 27.

In the case where the object 1 is comprised of an object to be checked for defects, an operator decides the kind of the object and sends the kind information, representing the kind of the object, to the system controller 22. The kind information is comprised of the information representing the kinds of fabrics in the case of the object being the fabric, the information on the CRT's screen size (14 inches, 21 inches, 29 inches, etc.), the information on the aspect ratio (4:3, 16:9, etc.) of the screen, and the information as to whether the CRT is a high definition use in the case of the object being the shadow mask of the color CRT, and the information on the panel size, number of pixels, etc., in the case of the object being the liquid crystal panel. Further, the operator can designate the field size of the image pickup device 4 to the object 1 through the console 23. When the designation is so made, the information of the field is input to the system controller. The field size is defined by:

The pixel size×the number of pixels÷imaging magnification. The pitch of the periodic pattern contained in the object differs in values depending upon the kinds of objects. The relation, that is, a relation between the kinds of objects to be checked and the basic pitch of the periodic pattern contained in the object, is initially determined and it is stored as a table in the ROM 24. Upon receipt of the kind information from the console 23 the system controller 22 reads out the pitch information of the periodic pattern corresponding to the kind information from the ROM 24 and, on the basis of the pitch information and information on the field size input from the console 23, sends an imaging magnification control signal 25 to the zoom driver 27. The zoom driver 27 sets the imaging magnification of the zoom lens 2 on the basis of the imaging magnification control signal 25 and, by doing so, sets the imaging magnification of the object 1 to the image pickup device 4. For this reason, the imaging magnification corresponds to the pitch information of the periodic pattern and information on the field size.

After the imaging magnification has been set, the system controller 22 slightly increases or decreases the imaging magnification control signal 25, on the basis of the result of the positive/negative determination, 21, from the positive/negative determination circuit 20 and the moire amount signal 17 from the moire amount detection circuit 10, so that the amount of moire is set below a setting value (detection limit). By doing so, the imaging magnification is finely adjusted. The practical algorithm for the fine adjustment of the imaging magnification will be explained below.

Figure 2:
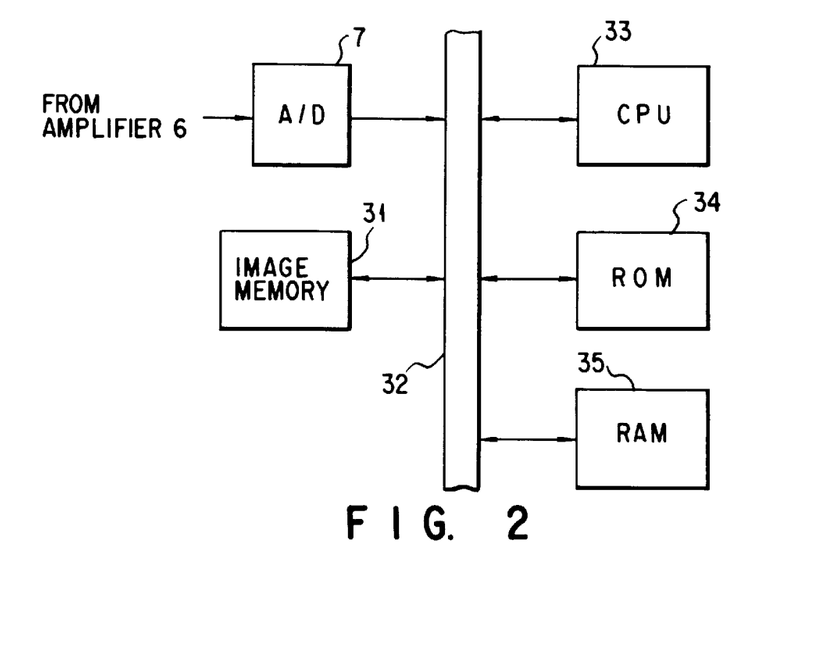
FIG. 2 is a block diagram showing a block diagram for realizing a major section of FIG. 1 by software processing.

Further, the monitor circuit 26 is provided in the present embodiment. The monitor circuit 26 informs a warming to the operator when the imaging magnification control signal 25 becomes such a value as to designate an off-normal magnification (for example, a magnification above the upper limit or below a lower limit of the zoom) to the zoom lens 2. Partial processing can be performed on the moire amount detection circuit 10, differentiating circuit 18, negative/positive determination circuit 20 and system controller 22 in FIG. 1 with the use of a software and, in the case, then that arrangement is as shown in FIG. 2. In FIG. 2, the image signal data output from the A/D converter 7 in FIG. 1 is once stored in an image memory 31 and input to a CPU 33 via a bus 32. In accordance with a program stored in ROM 34, the CPU 33 performs the processing, by the software, corresponding to the processing done on the moire amount detection circuit 10, differentiating circuit 18, negative/positive determination circuit 20 and system controller 22 in FIG. 1. A RAM 35 is comprised of a working memory for temporarily storing a result of part-calculation. Access can be gained not via the CPU 33 but via a DMA controller not shown. It is to be noted that the ROM 34 can be shared also as the ROM 24 in FIG. 1.

Figure 3:
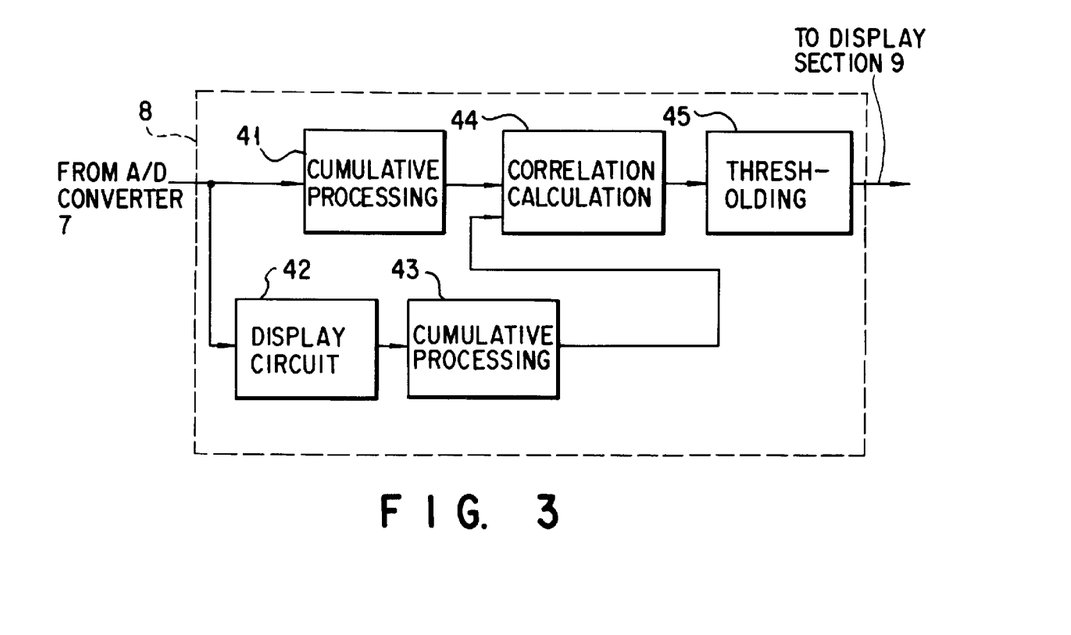
FIG. 3 is a block diagram showing a practical form of an image processing circuit in FIG. 1.

For the case of the defect checking apparatus, the image processing circuit 8 in FIG. 1 is so arranged as shown in FIG. 3. In FIG. 3, the image signal data from the A/D converter 7 in FIG. 1 is branched into two paths, one leading to a first cumulative processing circuit 41 and the other leading to a second cumulative processing circuit 43 via a delay circuit 42. The cumulative processing circuit 41 cumulates the data corresponding to a plurality (N) of continued pixels (N=100 for example) of input image signal data. The delay circuit 42 delays the input image signal by a shifting operation by an amount corresponding to, for example, N pixels and the second cumulative processing circuit 43 cumulates data of N pixels, like the first cumulative processing circuit 41, in the image signal output form the delay circuit 42. That is, these cumulative processing circuits 41 and 43, each, cumulate the N pixels delayed behind the amount corresponding to the N pixels. The results of cumulation by the cumulative processings 41 and 43 are input to a correlation calculation circuit 44 where an autocorrelation value of both, such as a difference or ratio, is found.

Through the autocorrelation processing of the correlation calculation circuit 44 in combination with the cumulative processing circuits 41, 43 and delay circuit 42 a defect in the object 1 is obtained as enhanced image data. On the image data output from the correlation calculation circuit 44, threshold processing is performed, by a threshold calculation circuit 45, with the use of a proper threshold value and, through this determination, it is possible to extract data corresponding to a defect spot.

For the case of the TV camera for broadcasting, etc., the image processing circuit 8 subjects the image signal from the A/D converter 7 simply to conversion processing to obtain a signal of a format determined by a desired TV standard system, such as an NTSC, PAL or HDTV.

The operation of the image pickup apparatus of the present embodiment will be explained below. First, an explanation will be given of a principle of detection by the moire amount detection circuit 10.

Figure 4:
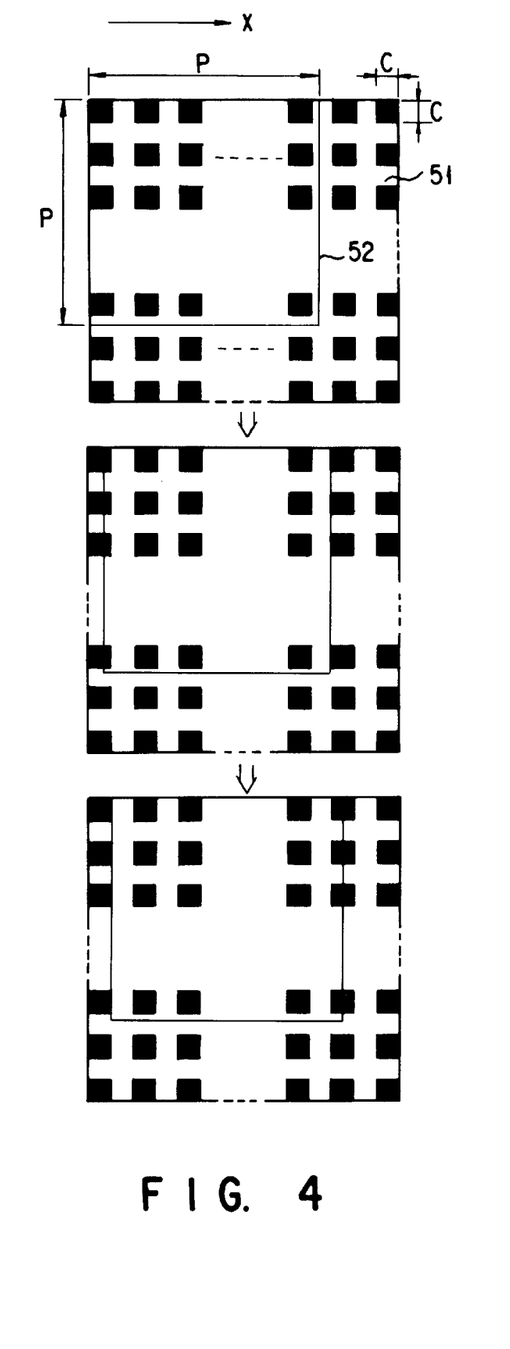
FIG. 4 is a view showing one example of a relation between pixels of an image pickup device and a periodic pattern used in the simulation of a moire pattern in the present invention.
Figure 5:
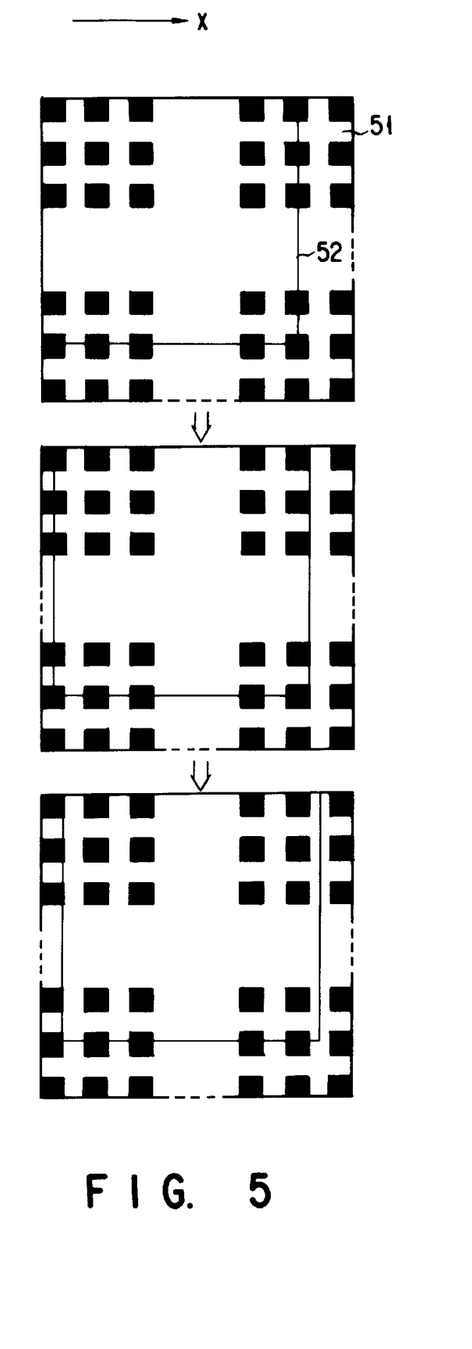
FIG. 5 is a view showing another example of a relation between pixels of an image pickup device and a periodic pattern used in the simulation of a moire pattern in the present invention.

A pattern 51 as shown in FIG. 4 or FIG. 5 is considered as a typical example of a periodic pattern in the object 1. The pattern 51 is prepared for simulating the generation of a moire pattern with very small solid squares (hereinafter referred to as black squares) formed at a 2C pitch in a white background, noting that one side of the flat square has a length C an 2C shows the pitch of the periodic pattern. Let it be supposed that such a pattern 51 is taken by the image pickup device 4. A square 52 shows a pixel of the image pickup device 4. Given that the size of the pixel 52 is represented by P×P (P hereinafter referred to as the pixel pitch), the case of FIG. 4 corresponds to $(2n-1)C \leq P \leq 2nC$ and the case of FIG. 5 corresponds to $2nC \leq P \leq (2n+1)C$, provided that n=any integer (1, 2, . . . ).

In this case, the luminance V of the image signal 5 output from the image pickup device 4 can be expressed by the following equation (1).

$$V = Zm\{1-(4S_B/P^2)\} \tag{1}$$

Here, Zm denotes the maximum luminance, that is, the pixel value of the image signal 5 corresponding to all white in the pixel 52 and "256" value of the output (8 bit data) of the A/D converter 7. $S_B$ represents a whole area of the black square in the pixel 52 and $P^2$, an area of the pixel 52.

When the luminance V is normalized by the maximum luminance Zm, a value D as shown in the following equation (2) is obtained. The value D is hereinafter referred to as a deviation value.

$$D = V/Zm = 1 - (4S_B/P^2) \qquad (2)$$

Figure 6:
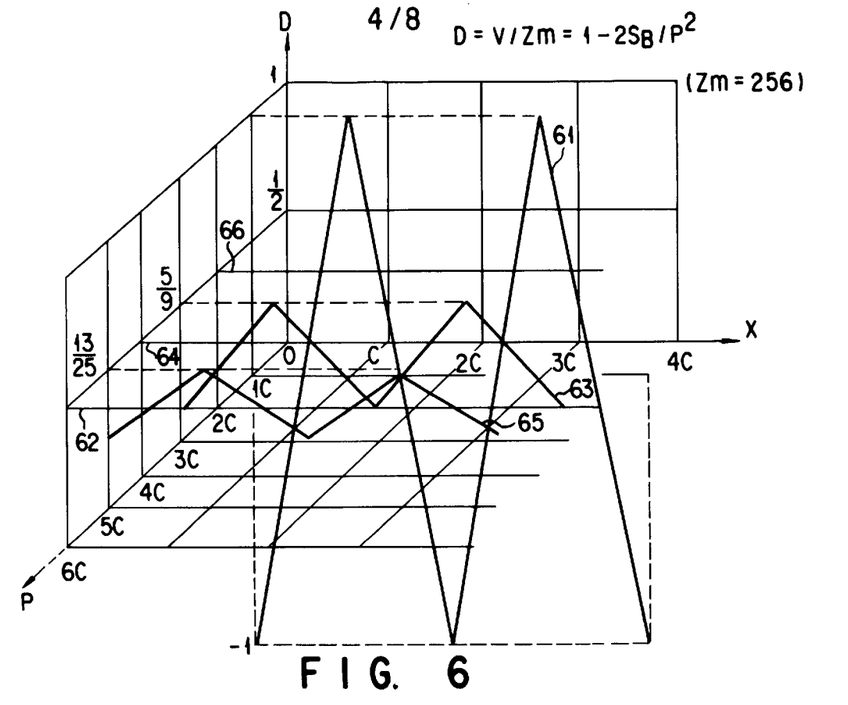

FIG. 6 shows a relation (variation), to the deviation value D, of an amount of X direction movement in the case where, with the pixel pitch P variously varied as C, 2C, 3C, 4C, 5C, 6C, . . . , the pixel 52 is moved in the X direction relative to the pattern 51 in conjunction with the perspective pixel pitch as indicated by arrows in FIG. 4 or 5. In FIG. 6, X shows a position of a left upper end of the pixel 52 on the pattern 51 in FIG. 4 or FIG. 5. The X-direction movement of the pixel 52 corresponds to the main scanning of the image pickup device 4.

As evident from FIG. 6, the deviation value D greatly varies with the X-direction movement of the pixel 52 in the case where P=C, 3C, 5C (characteristics 61, 63, 64), that is, the pixel pitch P is an odd multiple of the length of one side of the black square. This variation emerges as a moire pattern. On the other hand, the deviation value D becomes constant irrespective of the movement of the pixel 52 in the case where P=2C, 4C, 6C (characteristics 62, 64, 66), that is, the pixel pitch P is an even multiple (an integral multiple of the pitch 2C of the periodic pattern) of the length C of one side of the black square. There arises no moire pattern. When, in particular, the pixel pitch P has a two-times relation to the pitch of the periodic pattern imaged on the image pickup device, the highest resolution arises in a range producing no moire.

Figure 7:
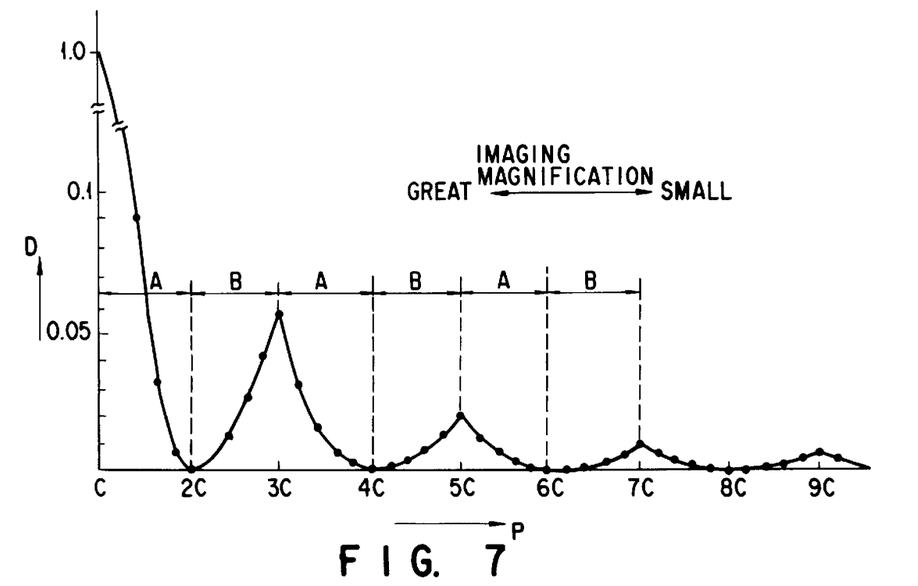
FIG. 7 shows a variation of a deviation value when the pixel pitch is varied with the pixel position fixed in FIG. 6.

FIG. 7 shows a variation of the deviation value D relative to a variation of the pixel pitch P in the case of X=C where the moire pattern is most liable to emerge.

From the result of the above simulation it is found that the moire pattern is eliminated by setting the pixel pitch P of the image pickup device 4 to be an integral multiple of the pitch 2C of the periodic pattern of the object 1 imaged on the image pickup device 4. However, even if there occurs the moire pattern no problem arises if it is to an extent not perceptible by human eye. It is, therefore, not necessary that a relation of the pixel pitch P of the image pickup device 4 to the pitch 2C of the periodic pattern be made exactly an integral multiple in real practice. To this end, in the embodiment of FIG. 1, an initially set imaging magnification may be so finely adjusted as to allow the moire pattern to be set to a limit not perceptible by human eye.

The relation of the pixel pitch P of the image pickup device 4 to the pitch of the periodic pattern of the object 1 imaged on the image pickup device 4 can be controlled by varying the imaging magnification of the object 1 relative to the image pickup device 4, that is, the magnification of the zoom lens 2. In FIG. 7 the direction in which the pixel pitch P is greater corresponds to that in which the imaging magnification is smaller in direction and the direction in which the pixel pitch P is smaller corresponds to that in which the imaging magnifications is greater in direction.

The moire amount detection circuit 10 in FIG. 1, delivers a moire amount signal 17 by finding the above-mentioned deviation value D by the normalization circuit 11, storing the image signal data of an interval corresponding to a plurality of continuous pixels, by the shift register 12, for example, the position of X=0 to 2C, finding a maximal value 14 and minimal value 15, by the maximum value/minimum value detection circuit 13, with respect to the image signal and finding a difference of these by the subtracter 16. That is, as clear from FIG. 6, at a moire pattern emerging area the luminance varies periodically at the period of below 2C and its variation amount, that is, the difference between the maximum value and the minimum value of the luminance, becomes greater in a way to correspond to the amount of moire, so that the amount of moire can be detected through the above-mentioned processing (by finding the difference of the maximum and minimum values during the 2C period) and it is possible to detect the amount of moire.

Although in the moire detection circuit 10 of FIG. 1, the amount of moire in the X direction only is detected in the case where the aspect ratio of the pitch of the periodic pattern on the object 1, that is, the X- and Y-direction pitches, are equal, it may be possible to detect the amount of moire also in the Y direction in the case where the aspect ratio of the pitch of the periodic pattern is other than 1:1, that is, the X- and Y-direction pitches are not equal to each other. In this case, the shift register 12 may be arranged in a plural array (N rows) so that it is possible to store image signal data corresponding to a plurality of continuous pixels in the Y-direction. Further, in the case where the TV camera takes natural images as an object, it is unclear what directionality the periodic pattern of the object possesses, that is, in which direction the moire pattern emerges. It is desirable to detect the amount of moire in the x and y directions and, further, it is effective to detect the amount of moire also in an oblique direction.

The practical procedure of controlling the imaging magnification in the present embodiment will be explained below.

Figure 8:
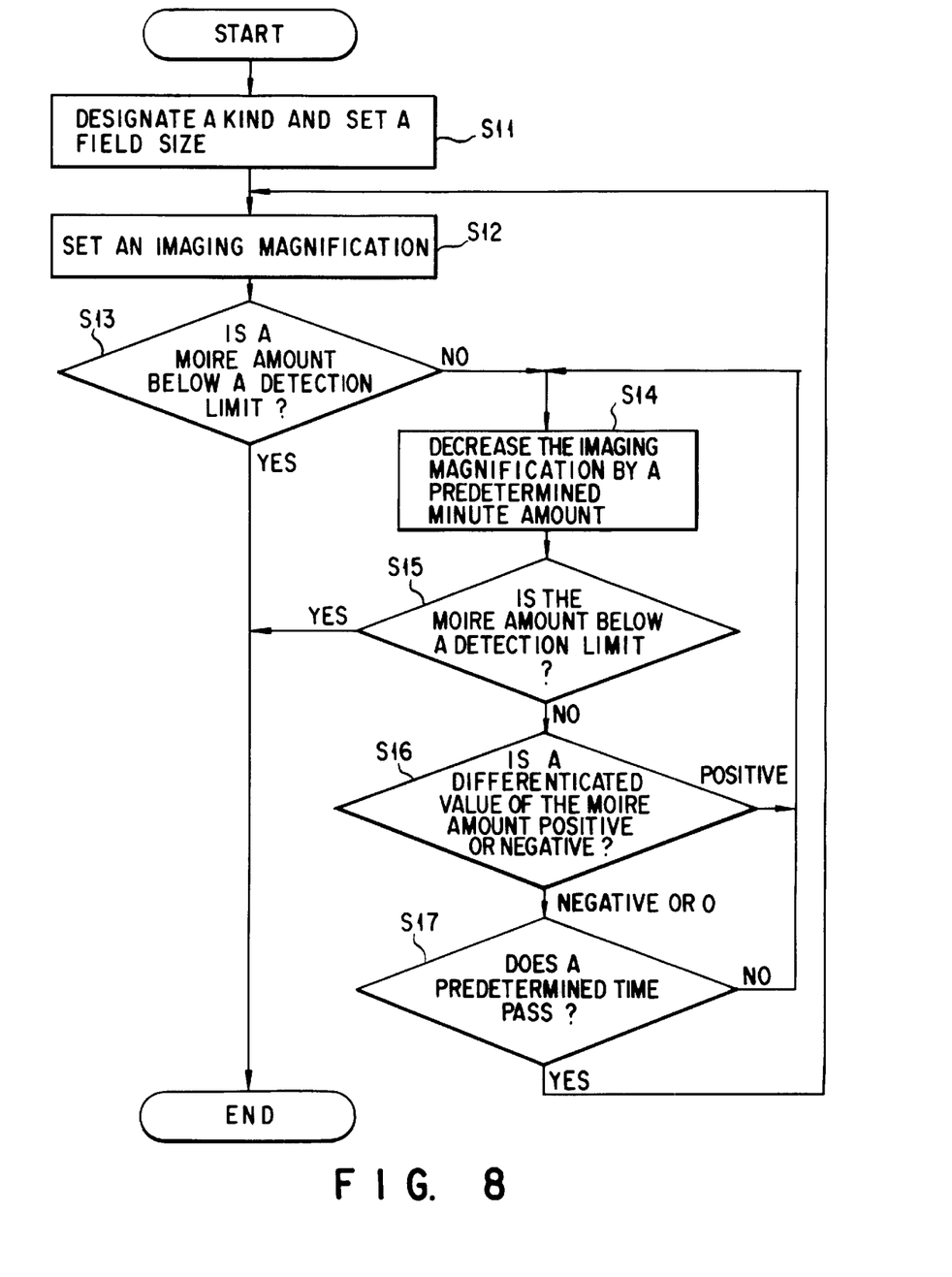
FIG. 8 is a flow chart showing one example of the procedure of controlling an imaging magnification in the embodiment.

FIG. 8 is a flow chart showing the procedure of controlling the imaging magnification suitable to the case where the present invention is applied to the defect checking apparatus, in particular, the case where the object to be checked has a random periodic pattern as that of the fabric.

When the operator sets the kind and field size of the object through the console 23 at step S11, at step S12 the system controller 22 sets the imaging magnification of the object relative to the image pickup device 4 in accordance with the pitch information read out from the ROM 24 and in a way corresponding to the kind of the object and the field size set at step S11. The imaging magnification is so set as to be as great as possible, so that microdefects can be detected with a higher resolution under the condition that the pixel pitch of the image pickup device 4 becomes an integral multiple of the pitch (=2C) of a basic periodic pattern on the object imaged on the image pickup device 4.

By doing so, the imaging magnification control signal 25 is supplied from the system controller 22 to the zoom driver 27 whereby the magnification of the zoom lens 2 is set.

Then at step S13, the system controller 22 checks whether or not the moire amount signal 17 output from the moire amount detection circuit 10 is below the setting value, that is, whether or not the amount of moire is below a detection limit. When the amount of moire is below the detection limit, the imaging magnification control is ended.

On the other hand, when at step S13 the amount of moire is determined to be not below the detection limit, the system controller 22 minutely decreases the magnification of the zoom lens 2 at step S14 by somewhat varying the imaging magnification control signal 25. That is, the fine adjustment is made stepwise in a direction to decrease the magnification. The reason that the magnification is decreased at the fine adjustment is because a visual field is secured for defect checking. That is, the decrease in the magnification leads to the increase in the vision of field.

Then at step S15 the system controller 22 checks whether or not the amount of moire is below the detection limit as in the case of step S13.

When the amount of moire is below the detection limit, the imaging magnification control is ended. When, on the other hand, the amount of moire is not below the detection limit at step S15 either, the positive/negative determining circuit 20 determines whether a differentiated value 19, that is, a variation caused by the fine adjustment of the imaging magnification of the moire amount signal 17 detected by the differentiating circuit 18 at step S16, is positive or negative (or zero).

Here, the case of the differentiated value 19 being positive means that, at FIG. 7, a deviation value D is located on the right side area B relative to a position 0 (for example, P=2C, 4C, . . . , position) as an optimal value and shifted in a direction away from the optimal point. On the other hand, the case of the differentiated value 19 being negative means that the deviation value D is located on the left hand side area A relative to the optimal point position and shifted toward the optimal point. Further, the case of the differentiated value 19 being 0 means that the deviation value D is located at a boundary between the area A and the area B, noting that this boundary is either at the optimal point or worst point (P=C, P=3C, . . . , position).

When the differentiated value 19 is positive as a result of determination at step S16, control is returned back to step S14. Until at step S15 the amount of moire is determined as being in a detection limit range or at step S16 the differentiated value 19 is determined as being negative or 0, the imaging magnification is decreased in given very small amounts. That is, in the case where the differentiated value 19 is positive, the differentiated value 19 becomes soon 0 or negative with a decreasing imaging magnification as seen from FIG. 7 and, thereafter, the amount of moire is decreased to the detection limit.

On the other hand, when the differentiated value 19 is negative or 0 as a result of determination at step S16, checking is made to see whether or not at step S17 the state of the amount of moire being above the detection limit is sustained in a predetermined time, that is, at step S14 the fine adjustment of the imaging magnification is effected a predetermined number of times. When the state above is sustained above the predetermined time, control is returned back to step S12 and re-setting of the imaging magnifications is carried out. Upon the resetting of the imaging magnification the imaging magnification is set to be smaller than that initially set at step S12 but in a range satisfying the condition of the integral multiple of the pitch 2C of the periodic pattern on the object imaged on the image pickup device 4. If, for example, the imaging magnification initially set is a value corresponding to P=2C, re-setting is effected to a value corresponding to P=4C. Further, if the imaging magnification initially set is a value corresponding to P=4C, the imaging magnification is so re-set as to correspond to P=6C.

As shown in FIG. 7, the variation of the deviation value D resulting from the fine adjustment of the image magnification before and after the optimal value (P=2C, 4C, 6C, . . . ) is greater at a greater imaging magnification area (for example, P=2C) and is smaller at a smaller imaging magnification are (P=4C, 6C, etc.). According to the present invention, the fine adjustment is made at a smaller imaging magnification and, therefore, it is easy to push the amount of moire below the detection limit.

As the imaging magnification is decreased, the resolution is lowered, thus lowering the detection capability per se relative to the microracks. If, however, there arises any moire pattern, any relative great defect cannot be distinguished from the moire pattern, failing to detect it. With this taken into consideration, it is advisable to reduce the moire pattern through the lowering of the image magnification even if the resolution is somewhat lowered.

And the above-mentioned processing is repeated hereinafter. As a result of the above-mentioned processing, the control is ended when the moire pattern is below the detection limit.

Figure 9:
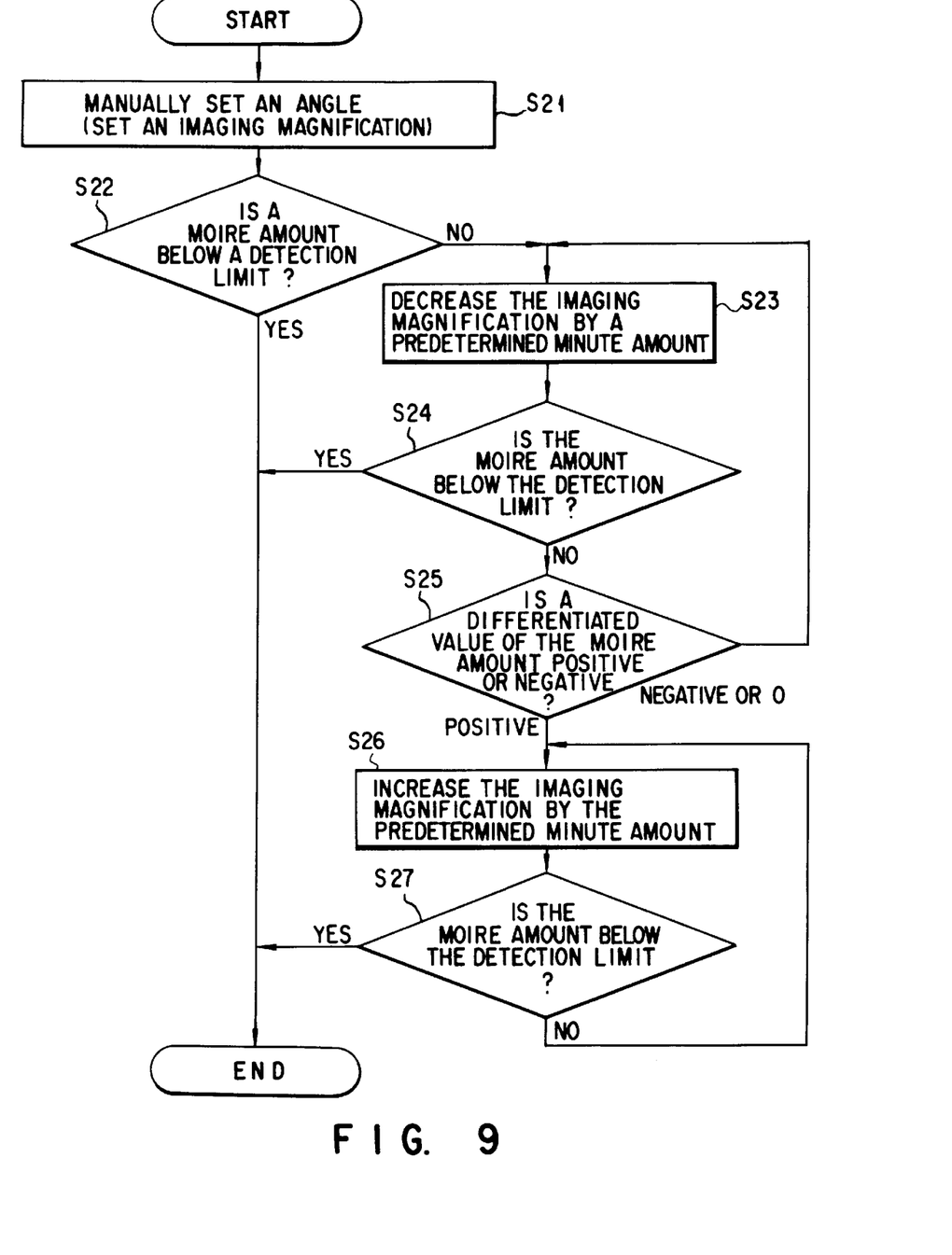
FIG. 9 is a flow chart showing another example of the procedure of controlling an imaging magnification in the present embodiment.

Then the procedure of controlling the imaging magnification when the present invention is applied to the TV camera for broadcasting for example will be explained below with reference to the flow chart as shown in FIG. 9.

First, at step S21, the operator (cameraman) of the TV camera manually sets the imaging angle to set the imaging magnification, that is, the magnification of the zoom lens 2. At step S22, determination is made as to whether or not the amount of moire detected by the moire amount detection circuit 10 is below the detection limit. Here, if the amount of moire is below the detection limit, the imaging magnification control is ended without making any fine adjustment of the imaging magnification.

When, on the other hand, the amount of moire is not below the detection limit, the imaging magnification is reduced by a predetermined very small amount at step S23 as in the case of the defect checking device as shown in FIG. 8 and then at step S24 determination is again made to see whether or not the amount of moire is below the detection limit. When, as a result of determination, the amount of moire is below the detection level, the imaging magnification control is ended and, when the amount of moire is not below the detection limit, a differentiated value 19 of the moire amount signal 17 is determined by the positive/negative determining circuit 20 at step S25 as to whether or not it is positive or negative (or 0).

When, as a result determination at step S25, the differentiated value 19 is negative or 0, control is returned back to step S23 and the imaging magnification is decreased in predetermined very small amounts until at step S24 the moire pattern is determined as being below the detection limit and at step S25 the differentiated value 19 is determined as being positive.

When at step S25 the differentiated value 19 is determined as being positive, the imaging magnification is increased, at step S26, by a predetermined very small amount and at step S27 determination is made to see whether or not the amount of moire is below the detection limit. When at step S27 the amount of moire is below the detection limit, the controlling of the imaging magnification is ended and, when the amount of moire is not below the detection limit, control is returned back to step S26 and, until the amount of moire becomes below the detection limit, the imaging magnification is increased by a predetermined very small amount.

It is not preferable, in the case of the TV camera, that the imaging angle intended by the cameraman is varied by the apparatus side so as to eliminate the moire pattern. In the case where, in the case of FIG. 9, unlike the case of FIG. 9, the amount of moire does not go below the detection limit even in the case where the imaging magnification is adjusted in predetermined very small amounts toward a decreasing direction, then reversely the imaging magnification is increased in predetermined very small amounts toward a greater direction and the amount of moire is pushed below the detection limit. That is, by finely adjusting the imaging magnification in the vicinity of the imaging magnification corresponding to an imaging angle intended by the cameraman, the moire pattern is reduced. It is to be noted that, since the adjusting amount of the imaging magnification for moire reduction has only to be very small, the angle never appears varied through this adjustment.

In the case where, in the TV camera for taking natural images, the amount of moire is detected, as set out above, in a plurality of directions, such as the x-, y- and oblique-directions, it is ideal to effect imaging magnification control as set out above so as to enable the amount of moire in all the directions to go below the detection limit. It is also effective that imaging magnification control be carried out, if that is not possible, so as to enable the amount of moire in an visually outstanding direction (for example, X-direction) to be lowered on a preferential way.

According to the present invention, it is possible to prevent occurrence of the moire pattern by setting the imaging magnification of the object imaged on the image pickup device in accordance with the pitch of the periodic pattern on the object so as to enable the pixel pitch to be made an integral multiple of the pitch of the periodic pattern imaged on the image pickup device.

Other embodiments of the present invention will be explained below.

Figure 10:
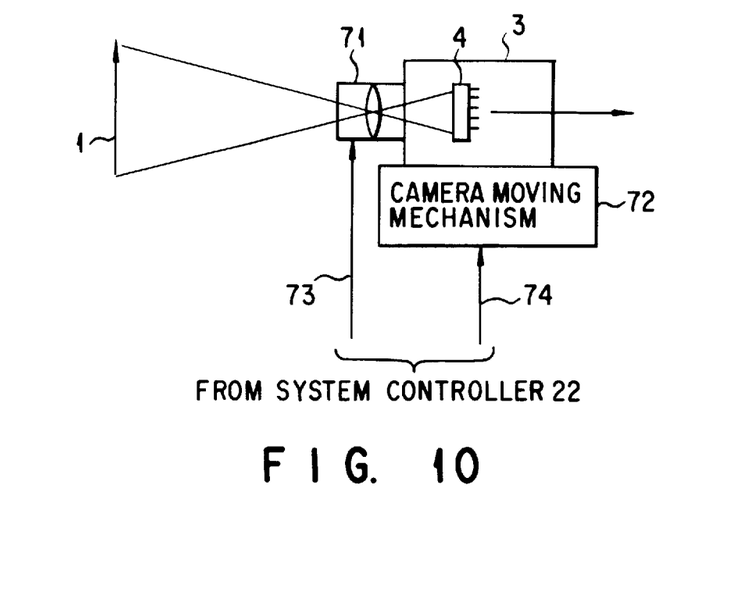
FIG. 10 is a view showing another example of an imaging magnification variable mechanism of the present invention.

Although, in the embodiment shown in FIG. 1, the zoom lens 2 has been explained as being used as the imaging magnification variable mechanism, the imaging magnification variable mechanism is not restricted thereto and, for example, it may be so configured as shown in FIG. 10 or 11.

In FIG. 10, a camera moving mechanism 72 is provided as to enable a camera section 3 to be moved in an optical axis direction (in a direction perpendicular to the imaging surface of an image pickup device 4) and imaging magnification is controlled by controlling the camera moving mechanism 72 from a system controller 22 side in FIG. 1 by an imaging magnification control signal 74. In this connection it is to be noted that the camera section 3, being moved toward the optical direction, goes out of focus relative to the image pickup device 4. Therefore, it is so configured that, by sending from the system controller 22 to an image taking lens 71 a focal control signal 73 varying in coincidence with the imaging magnification control signal 74, the distance between the image taking lens 71 and the image pickup device 4 is varied in interlock with the movement of the camera moving mechanism 72. In this case, as the image taking lens 71 use is made of a lens capable of adjusting the focal point under electronic control using, for example, a motor.

Figure 11A:
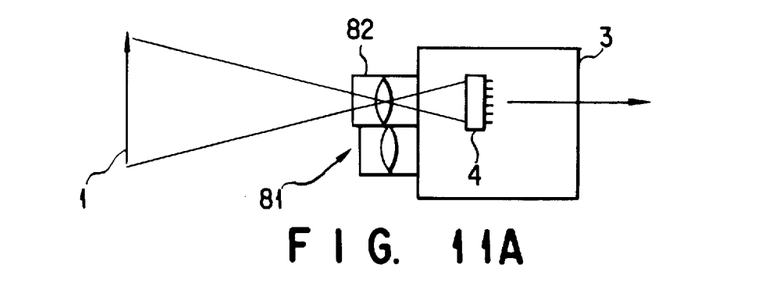
FIG. 11 is a view showing still another example of an imaging magnification variable mechanism of the present invention.
Figure 11B:
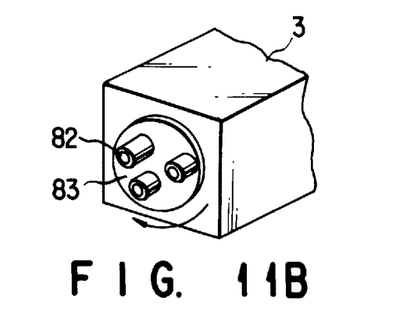
Figure 11C:
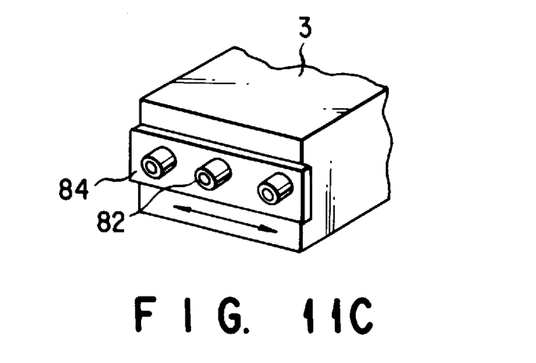

In the arrangement as shown in FIG. 11A, as an imaging optical system for forming an object imaging on an image pickup device 4 in the camera section 3, a lens exchange system 81 is used with a plurality of image taking lenses 82 of different focal points and an imaging magnification is made variable by selectively inserting image taking lenses 82, one having a structure as shown in FIG. 11B and one as shown in FIG. 11C, into an incident optical path of the image pickup device 4. In the example of FIG. 11B, a revolver type imaging magnification variable mechanism has a plurality of image taking lenses 82 arranged along a circumferential direction on a rotation disc 83 and is adapted to select one image taking lens by rotating the disc 83 in a direction as indicated as an arrow. Further, in the example of FIG. 11C, a linear type imaging magnification variable mechanism has a plurality of image taking lenses 82 arranged on a support plate 84 movable in a parallel way and is adapted to select one image taking lens by moving the support plate 84 in a direction as indicated by an arrow.

Further, as the imaging magnification variable mechanism it is possible to use the zoom lens 2 as shown in FIG. 1, camera moving mechanism 72 as shown in FIG. 10 and lens exchange system 81 as shown in FIG. 11 either selectively as the need arises or in any two or more component combination. It has been considered that, for example, the zoom lens is convenient to use as the imaging magnification variable mechanism of the present invention because it can vary the magnification without basically varying the focal point, but that the zoom lens is complex in lens structure, low in brightness and generally great in aberration. According to the arrangement as shown in FIG. 10 it is possible to eliminate the disadvantages involved in the case where the zoom lens is used. On the other hand, the camera moving mechanism 72, increasing its variable range, involves a bulkier mechanism. Using the zoom lens 2 and camera moving mechanism 72 in combination eliminates this disadvantage and, since as the zoom lens 2 use can be made of one having a narrow magnification variable range, it is possible to alleviate the disadvantage possessed by the zoom lens.

In the image magnification variable mechanism for selecting the imaging lens as shown in FIGS. 11B and 11C, it is not possible to effect fine adjustment of the imaging magnification but, for the object with a periodic pattern of a stable pitch, such as the shadow mask and liquid crystal panel, it is considered unnecessary to make fine adjustment of the imaging magnification, so that such a stepwise imaging magnification variable mechanism may be used.

Figure 12:
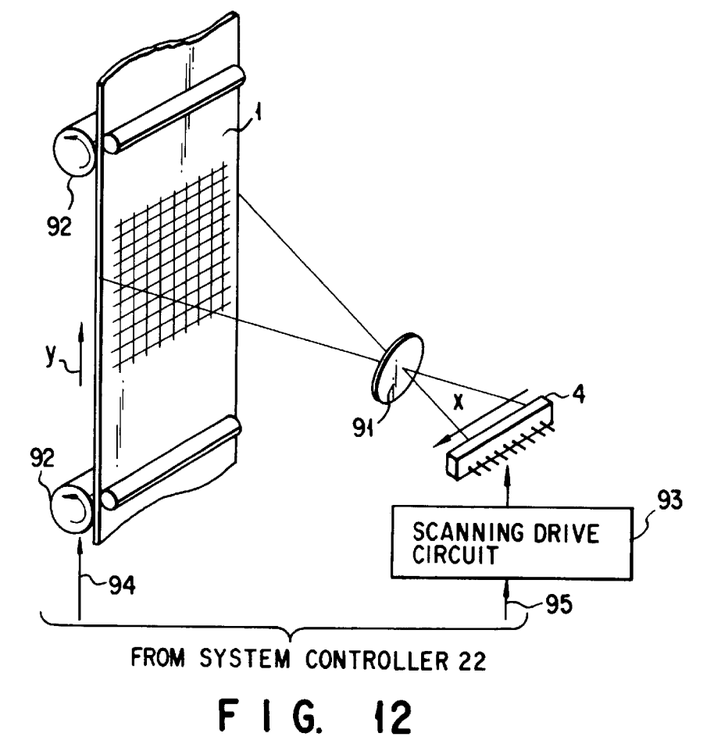
FIG. 12 is a view showing a schematic example of an aspect ratio correction mechanism at an image pickup optical system in the case where an aspect ratio of a periodic pattern on the object is not 1:1 in the present invention.
Figure 13:
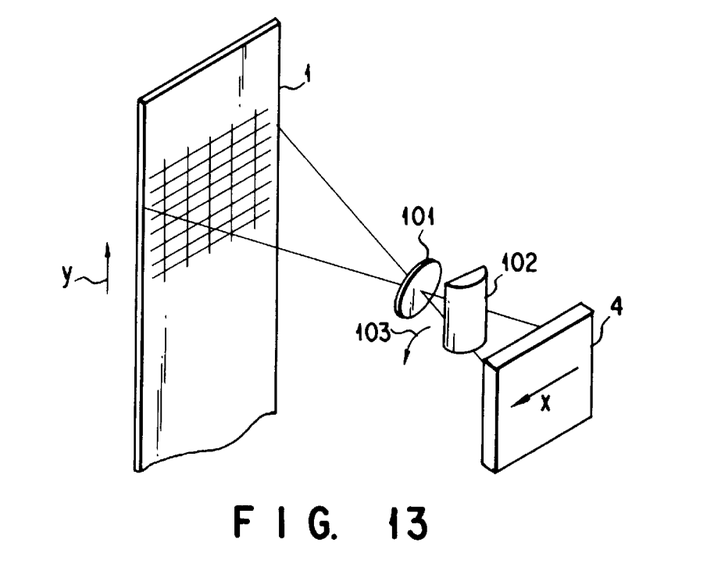
FIG. 13 is a view showing another example of aspect ratio correction mechanism at an image pickup optical system in the case where the aspect ratio of the periodic pattern on the object is not 1:1 in the present invention.

An explanation will be given below of the case where the periodic pattern pitch of the object 1 has an aspect ratio of not 1:1. The periodic pattern contained in the object, such as the fabric and liquid crystal panel, is not always equal in the aspect ratio's pitch and often differs is the aspect ratio's pitch. The above-mentioned imaging magnification variable mechanism, of course, including the zoom lens, makes the imaging magnification variable at the 1:1 aspect ratio and, if the aspect ratio of the pitch of the periodic pattern in the object is not 1:1, correction is required so that the aspect ratio of the pitch of the periodic pattern on the image signal output from the image pickup device 4 may be made at 1:1, that is, the aspect ratio per pixel of an image formed on the image pickup device 4 may be made at 1:1. FIG. 12 and FIG. 13 each show an example of such aspect ratio correcting mechanism.

FIG. 12 shows an example of the image pickup device being a one-dimensional array sensor. An image of one line of an object 1 is formed by an image taking lens 91 on an image pickup device 4. The object 1 is made of a lengthy sheet as shown in FIG. 12 and moved by a moving mechanism 92 in a direction (sub scanning direction) as indicated by an arrow y, the mechanism 92 being comprised of a roller set, etc. The moving mechanism 92 is so driven as to allow the object 1 to be moved with a speed (sub scanning speed) corresponding to a sub scanning synchronization signal 94 from the system controller 22 in FIG. 1. The image pickup device 4 is scanned by the scanning drive circuit 93 in a direction (main scanning direction) of a sensor as indicated by an arrow x and an image signal corresponding to one line is output in a serial fashion in accordance with the main scanning. The period of the main scanning is controlled by a main scanning synchronization signal 95.

Given here that the aspect ratio of the pitch of the periodic pattern on the object 1 is N:1 (N:a positive integer exceeding unity), the above-mentioned sub scanning speed is made an N times its aspect ratio or the main scanning period is made at a 1/N ratio. By doing so, if N=2 for example, the main scanning over one period of the image pickup device 4 is ended while the object 1 is moved in the sub scanning direction by a distance corresponding to two pixels. By doing so, the aspect ratio of the pitch of the periodic pattern on the image signal output from the image pickup device 4, that is, the aspect ratio per pixel of an image formed on the image pickup device 4 becomes 1:1.

FIG. 13 shows an example of an image pickup device 4 being a two-dimensional sensor. An image of an object 1 is formed on the image pickup device 4 by a convex lens 101 and cylindrical lens 102 and the aspect ratio per pixel is corrected by the cylindrical lens 102.

That is, in the case where the aspect ratio of the pitch of the periodic pattern on the object 1 is 1:N (N:a positive number exceeding unity), if the axis of the cylindrical lens 102 is aligned with a y direction, an image formed on the image pickup device 4 is compressed in an x direction. By properly selecting the curvature of the cylindrical lens 102 the aspect ratio per pixel of an image formed on the image pickup device 4 is corrected to 1:1. In the case where, on the other hand, the aspect ratio of the pitch of the periodic pattern on the object 1 is N:1 (N:a positive number exceeding unity), if the axis of the cylindrical lens 102 is rotated in a direction to be aligned with the x direction, an image formed on the image pickup device 4 is compressed in the y direction and, by properly selecting the curvature of the cylindrical lens 102, the aspect ratio per pixel of an image formed on the image pickup device 4 is corrected to 1:1.

By taking such an aspect ratio correcting mechanism in combination with the image pickup device in FIG. 1, it is possible to detect the above-mentioned moire amount even in the case where the aspect ratio of the pitch of the periodic pattern on the object 1 is not 1:1.

The present invention is not restricted to the above-mentioned embodiment and various changes and modifications can be made. For example, the present image pickup apparatus is not restricted as an application apparatus to the defect checking apparatus, etc., and can be applied to anything if it is directed to taking an image of an object including a periodic pattern. Although the aspect ratio of the pitch of the periodic pattern has been explained as being 1:1, it is not necessarily required to be 1:1.

INDUSTRIAL APPLICABILITY

As already set out above, an image pickup apparatus of the present invention can take an image from an object having a periodic pattern with high precision while eliminating a moire pattern and be properly applied to a defect checking apparatus and a TV camera for broadcasting, etc.

We claim:

1. An image pickup apparatus comprising:
   image pickup means for taking an image from an object containing a periodic pattern and for outputting an image signal;
   image processing means for processing the image signal output from said image pickup means; and
   magnification setting means for setting an imaging magnification of the object relative to the image device in accordance with a pitch of a periodic pattern contained in the object,
   wherein said magnification setting means comprises means for setting the image magnification to allow a pixel pitch of said image pickup means to be made an integral multiple of the pitch of the periodic pattern imaged on said image pickup means.

2. The image pickup apparatus according to claim 1, wherein said magnification setting means comprises means for setting the image magnification to allow the pixel pitch of the image pickup means to be made double the pitch of the periodic pattern imaged on said image pickup means.

3. The image pickup apparatus according to claim 1, wherein said magnification setting means comprises a zoom lens arranged in an incident optical path of said image pickup means and means for adjusting the magnification of the zoom lens.

4. The image pickup apparatus according to claim 1, wherein said magnification setting means comprises means for adjusting a distance between the object and said image pickup means.

5. The image pickup apparatus according to claim 1, wherein said magnification setting means comprises plural lenses having different focal lengths and means for selectively inserting one of said plural lenses into an incident optical path of said image pickup means.

6. The image pickup apparatus according to claim 1, wherein said magnification setting means comprises memory means for storing a relation of the kind of objects to the pitch of the periodic pattern contained in the object and means for setting the imaging magnification on the basis of the pitch read out from the memory means in accordance with the kind of the object.

7. The image pickup apparatus according to claim 1, wherein said image processing means comprises means for detecting a defect spot in the object.

8. The image pickup apparatus according to claim 1, further comprising aspect ratio correcting means for varying an aspect ratio per pixel of the image formed on said image pickup means by controlling at least one of a scanning speed of said image pickup means and a moving speed of the object relative to said image pickup means in accordance with the aspect ratio of the pitch of the periodic pattern contained in the object.

9. The image pickup apparatus according to claim 1, further comprising aspect ratio correcting means for optically varying an aspect ratio per pixel of the image formed on said image pickup means in accordance with the aspect ratio of the pitch of the periodic pattern contained in the object.

10. An image pickup apparatus comprising:
    image pickup means for taking an image from an object containing a periodic pattern and for outputting an image signal;
    image processing means for processing the image signal output from said image pickup means;
    means for detecting an amount of moire on the basis of the image signal output from said image pickup means; and
    magnification setting means for setting an imaging magnification of the object relative to said image pickup means so that the amount of moire detected by the detecting means becomes below a setting amount,
    wherein said magnification setting means comprises means for setting the image magnification to allow a pixel pitch of said image pickup means to be made an integral multiple of a pitch of the periodic pattern imaged on said image pickup means.

11. The image pickup apparatus according to claim 10, wherein said magnification setting means comprises means for setting the image magnification to allow the pixel pitch of said image pickup means to be made double the pitch of the periodic pattern imaged on said image pickup means.

12. The image pickup apparatus according to claim 10, wherein said magnification setting means comprises a zoom lens arranged in an incident optical path of said image pickup means and means for adjusting the magnification of the zoom lens.

13. The image pickup apparatus according to claim 10, wherein said magnification setting means comprises means for adjusting a distance between the object and said image pickup means.

14. The image pickup apparatus according to claim 10, wherein said magnification setting means comprises a plurality of lenses of different focal distances and means for selectively inserting any one of the plurality of image taking lenses in an incident optical path of said image pickup means.

15. The image pickup apparatus according to claim 10, wherein said magnification setting means comprises memory means for storing a relation of kinds of objects to the pitch of the periodic pattern contained in the object and means for setting the imaging magnification on the basis of the pitch read out from the memory means in accordance with the kind of the object.

16. The image pickup apparatus according to claim 10, wherein said image processing means comprises means for detecting a defect spot in the object.

17. The image pickup apparatus according to claim 10, further comprising aspect ratio compensating means for varying an aspect ratio per pixel of the image formed on said image pickup means by controlling at least one of a scanning speed of said image pickup means and moving speed of the object relative to said image pickup means in accordance with the aspect ratio of the pitch of the periodic pattern contained in the object.

18. The image pickup apparatus according to claim 10, further comprising aspect ratio correcting means for optically varying an aspect ratio per pixel of the image formed on said image pickup means in accordance with the aspect ratio of the pitch of the periodic pattern contained in the object.

19. The image pickup apparatus according to claim 10, wherein said magnification setting means comprises means for re-setting an imaging magnification when the amount of moire detected by the detecting means is not below the setting amount.

20. The image pickup apparatus according to claim 10, wherein said detecting means comprises means for detecting the amount of moire by finding a difference between a maximal value and minimal value of a predetermined range of the image signal.

* * * * *